United States Patent [19]

Lutz

[11] Patent Number: 5,281,366
[45] Date of Patent: * Jan. 25, 1994

[54] PROCESS FOR THE PREPARATION OF SECONDARY ALKYL SULFATE-CONTAINING SURFACTANT COMPOSITIONS

[75] Inventor: Eugene F. Lutz, Houston, Tex.

[73] Assignee: Shell Oil Company, Houston, Tex.

[*] Notice: The portion of the term of this patent subsequent to Dec. 24, 2008 has been disclaimed.

[21] Appl. No.: 946,120

[22] Filed: Sep. 17, 1992

[51] Int. Cl.$^5$ .................. C11D 1/14; C11D 1/83; C11D 3/32; C11D 11/04

[52] U.S. Cl. .................. 252/550; 252/549; 252/174.21; 558/39; 558/41; 558/42; 558/43

[58] Field of Search .................. 252/550, 549, 174.21; 558/39, 41, 42, 43

[56] References Cited

U.S. PATENT DOCUMENTS

| | | |
|---|---|---|
| 2,094,546 | 9/1937 | Lyons . |
| 2,640,070 | 5/1953 | Dahmen . |
| 2,945,818 | 7/1960 | Costine et al. . |
| 3,234,258 | 2/1966 | Morris . |
| 3,676,523 | 7/1972 | Mason . |
| 3,681,424 | 8/1972 | Bloch et al. . |
| 3,686,351 | 8/1972 | Mason . |
| 3,737,475 | 6/1973 | Mason . |
| 3,825,615 | 7/1974 | Lutz . |
| 3,893,940 | 7/1975 | Ohogoshi et al. . |
| 4,021,121 | 4/1977 | Kister et al. . |
| 4,052,342 | 10/1977 | Fernley et al. . |
| 4,088,598 | 5/1978 | Williams . |
| 4,226,797 | 10/1980 | Bakker et al. . |
| 4,317,938 | 3/1982 | Lutz .................. 558/42 |
| 4,474,678 | 10/1984 | Lutz et al. . |
| 4,488,934 | 12/1984 | Silvis .................. 202/234 |
| 4,544,493 | 10/1985 | Silvis . |
| 4,857,213 | 8/1989 | Caswell et al. . |
| 5,075,041 | 12/1991 | Lutz . |

FOREIGN PATENT DOCUMENTS

| | | |
|---|---|---|
| 884656 | 12/1961 | United Kingdom . |
| 1194862 | 6/1970 | United Kingdom . |
| 1585030 | 5/1978 | United Kingdom . |

OTHER PUBLICATIONS

Asinger, "The Hydration of Olefins to Alcohols," Mono-olefins: Chemistry and Technology, 1968, pp. 689–704.

Primary Examiner—Paul Lieberman
Assistant Examiner—Bradley A. Swope
Attorney, Agent, or Firm—Pamela J. McCollough

[57] ABSTRACT

This invention relates to a process for preparing secondary alkyl sulfate-containing surface active compositions substantially free of unreacted organic matter and water, which process comprises: a) sulfating a mixture of a detergent range olefin having from about 8 to about 22 carbon atoms and a detergent range alcohol having from about 8 to about 22 carbon atoms with a sulfating agent, b) neutralizing the product of step a) with a base dispersed in a nonionic surfactant having a boiling point higher than that of said detergent range olefin and its corresponding secondary alcohol, c) saponifying the product of step b), d) passing the product of step c) through a thin film evaporator to evaporate unreacted organic matter from said product and recovering said product.

32 Claims, No Drawings

PROCESS FOR THE PREPARATION OF SECONDARY ALKYL SULFATE-CONTAINING SURFACTANT COMPOSITIONS

FIELD OF THE INVENTION

This invention relates to a process for the preparation of secondary alkyl sulfate-containing surfactant compositions.

BACKGROUND OF THE INVENTION

This invention provides a process for preparing surfactant compositions containing secondary alkyl sulfates which are substantially free of unreacted organic matter (UOM), and which are substantially free of water, thus making the compositions substantially free of inert diluents.

In conventional practice, secondary alkyl sulfates have been derived from both olefins and alcohols using sulfuric acid, followed by neutralization of the intermediate secondary alkyl sulfuric acid with the appropriate base, although olefin-derived secondary alkyl sulfates have not been as extensively investigated as alcohol-derived secondary alkyl sulfates. The process is complicated by incomplete reaction of the starting olefin and alcohol and by formation of dialkyl sulfates which saponify during the neutralization step, noted above, to equal molar amounts of secondary alkyl sulfate and secondary alcohol.

Unreacted olefin and secondary alcohol, which can amount to 50% by weight or more of the starting olefin, are generally removed from the secondary alkyl sulfate by a process of extraction with an organic solvent as described in U.S. Pat. No. 4,175,092. The extraction process can be complicated by the formation of undesirable emulsions and gels as well as by the dissolution of some of the extracting solvent in the aqueous secondary alkyl sulfate phase. Extracting solvents frequently have objectionable odors and must be removed from the aqueous surfactant solution, an operation which can be accompanied by severe foaming difficulties. When extraction is complete, the concentration of secondary alkyl sulfate in water is generally in the range of 20-40% by weight (F. Asinger, *Mono-Olefins: Chemistry and Technology*, 1968, pp. 689-694).

It would therefore be advantageous to have a process for preparing surfactant compositions utilizing secondary alkyl sulfates as the anionic component which eliminates the problems associated with solvent extraction for removal of the non-surface active organic material and which produces a product free of water, thus allowing maximum handling and blending flexibility.

An integrated process for preparing surfactant compositions has been found in which secondary alkyl sulfates derived from a mixture of olefins and alcohols can be generated in a manner such that the non-surface active material can be easily stripped from the secondary alkyl sulfates while at the same time producing a surfactant and/or detergent composition which is particularly useful for household applications.

It is therefore an object of this invention to prepare surface active compositions containing secondary alkyl sulfates derived from a mixture of olefins and alcohols, which are substantially free of unreacted olefin and substantially free of water, in a nonionic surfactant having a boiling point higher than the olefin reaction and its corresponding secondary alcohol. In the present invention, a surface active composition is prepared by reacting a mixture of one or more detergent range alcohols and one or more detergent range olefins with a sulfating agent, removing excess sulfating agent, neutralizing and saponifying the mixture in the presence of a base dispersed in a nonionic surfactant having a boiling point higher than the detergent range olefin and its corresponding secondary alcohol, and then passing the mixture through a falling film or wiped film evaporator to strip unreacted organic matter from the mixture, thereby producing a secondary alkyl sulfate-containing detergent composition which is anhydrous and substantially free of inert diluents.

SUMMARY OF THE INVENTION

This invention relates to a process for preparing secondary alkyl sulfate-containing surface active compositions substantially free of unreacted organic matter and water, which process comprises: a) sulfating a mixture of a detergent range alcohol having from about 8 to about 22 carbon atoms and a detergent range olefin having from about 8 to about 22 carbon atoms with a sulfating agent, and, optionally, removing excess sulfuric acid by water wash, b) neutralizing the product of step a) with a base dispersed in a nonionic surfactant having a boiling point higher than said detergent range olefin and its corresponding secondary alcohol, c) saponifying the product of step b), d) passing the product of step c) through a thin film evaporator to evaporate unreacted organic matter from said product and recovering said product. The unreacted organic matter evaporated from the product can be recycled, if desired.

DESCRIPTION OF THE PREFERRED EMBODIMENTS

This invention relates to secondary alkyl sulfate-containing surface active compositions substantially free of unreacted organic matter and water prepared by a process which comprises sulfation of a mixture of a detergent range alcohol and a detergent range olefin by adding a sulfating agent followed by water washing to remove excess sulfating agent, neutralization with a base dispersed in a nonionic surfactant having a boiling point higher than that of said detergent range olefin and its corresponding secondary alcohol, saponification, and then distillation of unreacted organic matter, thus generating a surfactant composition comprising secondary alkyl sulfate and nonionic surfactant.

As used herein, the phrase "substantially free of unreacted organic matter and water" refers to detergent compositions which contain less than about 10 percent by weight, preferably less than about 5 percent by weight, of unreacted organic matter and less than about 5 percent by weight, preferably less than about 2 percent by weight, of water.

The detergent range olefins which are sulfated in step a) of the instant invention are olefins containing from about 8 to about 22 carbon atoms. These olefins can be alpha olefins or internal olefins and they may be linear or branched, but are preferably linear or lightly branched. Single cut olefins or mixtures of olefins may also be used. In a particularly preferred embodiment, the olefin contains from about 12 to about 18 carbon atoms.

Preferred for use as olefin reactants for the practical reason of availability are the commercial olefin products in the $C_8$ to $C_{22}$ range. While commercial production of such olefins may be carried out by the cracking of paraffin wax, commercial production is more commonly accomplished by the oligomerization of ethylene using procedures well known in the art. The resulting oligomerization products are substantially of linear structure and thus products are substantially of linear structure. Commercial olefin products manufactured by ethylene oligomerization are marketed in the United States by Shell Chemical Company under the trademark Neodene and by Ethyl Corporation as Ethyl Alpha-Olefins. Specific procedures for preparing suitable linear olefins from ethylene are described in U.S. Pat. Nos. 3,676,523, 3,686,351, 3,737,475, 3,825,615 and 4,020,121, the teachings of which are incorporated herein by reference. While most of such olefin products are comprised largely of alpha-olefins, higher linear internal olefins are also commercially produced, for example, by the chlorination-dehydrochlorination of paraffins, by paraffin dehydrogenation, and by isomerization of alpha-olefins. Linear internal olefin products in the $C_8$ to $C_{22}$ range are marketed by Shell Chemical Company and by Liquichemica Company. These commercial products, whether predominantly internal or alpha-olefins typically contain about 70 percent by weight or more, most often about 80 percent by weight or more, linear mono-olefins in a specified carbon number range (e.g., $C_{10}$ to $C_{12}$, $C_{11}$ to $C_{15}$, $C_{12}$ to $C_{13}$, $C_{15}$ to $C_{18}$, etc.) the remainder of the product being olefin of other carbon number or carbon structure, diolefins, paraffins, aromatics, and other impurities resulting from the synthesis process. Olefins marketed in the United States in the $C_{12}$ to $C_{18}$ range are considered most preferred for use in the instant invention.

The detergent range alcohols which are suitable for use in the present invention are alcohols containing from about 8 to about 22 carbon atoms. Acyclic aliphatic alcohols having from about 9 to about 18 carbon atoms form a preferred class of reactants, particularly the secondary alcohols, although primary alcohols can also be utilized. As a general rule, the carbon chains of the alcohols may be of either branched or linear (straight-chain) structure, although alcohol reactants in which greater than about 50 percent, more preferably greater than about 70 percent and most preferably greater than about 90 percent of the molecules are of linear (straight-chain) carbon structure are preferred. In large part, such preferences relate more to the utility and value of the products than to the operability or performance of the process of the invention.

Specific examples of branched chain or secondary alcohols include 2-hexadecanol, hexadecanols, tetradecanols and the like. Commercially available mixtures of secondary alcohols prepared via the oxidation of paraffins, and from internal olefins and alpha-olefins mixtures via sulfation and hydrolysis reactions are also suitable. Specific examples of commercially available secondary alcohol mixtures include Tergitol 15, a trademark of and sold by Union Carbide, in which the main components are $C_{11}$ to $C_{15}$ compounds; Tergitol 45, in which the main components are $C_{14}$ to $C_{15}$ compounds; Softanol 24, a trademark of and sold by Nippon Shokubai Kagaku Kogyo Co., Ltd., in which the main components are $C_{12}$ to $C_{14}$ compounds, and the like.

Specific examples of suitable primary straight-chain monohydric aliphatic alcohols include dodecanol, pentadecanol, octadecanol, eicosanol and the like. Mixtures of alcohols are also suitable for purposes of the invention and are often preferred for reasons of commercial availability. Commercially available mixtures of primary monoalcohols prepared via the oligomerization of ethylene and the hydroformylation or oxidation and hydrolysis of the resulting higher olefins are particularly preferred. Specific examples of commercially available alcohol mixtures in the $C_9$ to $C_{20}$ range include the NEODOL Alcohols, trademark of and sold by Shell Chemical Company, including mixtures of $C_9$, $C_{10}$ and $C_{11}$ alcohols (NEODOL 91 Alcohol), mixtures of C12 and C13 alcohols (NEODOL 23 Alcohol), mixtures of $C_{12}$, $C_{13}$, $C_{14}$, and $C_{15}$ alcohols (NEODOL 25 Alcohol), and mixtures of C 14 and C·15 alcohols (NEODOL 45 Alcohol); the ALFOL Alcohols, trademark of and sold by Vista Chemical Company, including mixtures of $C_{10}$ and $C_{12}$ alcohols (ALFOL 1012), mixtures of $C_{12}$ and C14 alcohols (ALFOL 1214), mixtures of $C_{16}$ and $C_{18}$ alcohols (ALFOL 1618), and mixtures of $C_{16}$, $C_{18}$ and $C_{20}$ alcohols (ALFOL 1620); the EPAL Alcohols, trademark of and sold by Ethyl Chemical Company, including mixtures of $C_{10}$ and $C_{12}$ alcohols (EPAL 1012), mixtures of $C_{12}$ and $C_{14}$ alcohols (EPAL 1214), and mixtures of $C_{14}$, $C_{16}$, and $C_{18}$ alcohols (EPAL 1418); and the TERGITOL-L Alcohols, trademark of and sold by Union Carbide Corporation, including mixtures of C 12, C13, C14, and C15 alcohols (TERGITOL 125). Also very suitable are the commercially available alcohols prepared by the reduction of naturally occurring fatty esters, for example, the CO and TA products of Procter and Gamble Company and the TA alcohols of Ashland Oil Company.

As used herein, the term "alcohol reactant" is also intended to include alcohol ethoxylates such as, for example, ethoxylated fatty alcohols, preferably linear primary or secondary monohydric alcohols with about $C_8$ to about $C_{22}$, preferably about $C_{12}$ to about $C_{15}$, alkyl groups and an average of about 0.5 to about 15, preferably about 0.5 to about 9, moles of ethylene oxide per mole of alcohol, and ethoxylated alkylphenols with $C_8$ to about $C_{12}$ alkyl groups, preferably about $C_8$ to about $C_{10}$ alkyl groups and an average of about 1 to about 12 moles of ethylene oxide per mole of alkylphenol.

In a preferred embodiment, the alcohol reactant is a primary alcohol, preferably selected from the group consisting of dodecanol, tridecanol and their corresponding low molecular weight ethoxylates and mixtures thereof, with a blend of $C_{12}$ to $C_{13}$ alcohols to which one mole of ethylene oxide per mole of alcohol has been added being particularly preferred. The sulfating agents suitable for use in sulfating the mixture of detergent range olefins and detergent range alcohols in step a) include those compounds capable of forming the carbon to oxygen to sulfur bonds necessary for the formation of an alkyl sulfate. These sulfating agents are known in the art and typically include sulfuric acids and sulfuric acid salts. In a preferred embodiment, the sulfating agent is concentrated sulfuric acid. The concentrated sulfuric acid typically has a concentration of from about 75 percent by weight to about 100 percent by weight, preferably from about 85 percent by weight to about 98 percent by weight, in water. Suitable amounts of sulfuric acid are generally in the range of from about 0.3 moles to about 1.3 moles of sulfuric acid per mole of olefin and alcohol and from about 0.4 moles to about 1.0 mole of sulfuric acid per mole of olefin and alcohol.

The sulfation reaction in step a) is suitably carried out at temperatures in the range of from about −20° C. to about 50° C., preferably from about 5° C. to about 40° C., and at pressures in the range of from about 1 atmosphere to about 5 atmospheres, preferably from about 1 atmosphere to about 2 atmospheres, and more preferably, about 1 atmosphere. Suitable residence times for the sulfation reaction range from a few minutes to several hours, preferably from about 2 minutes to about 10 hours and more preferably, from about 5 minutes to about 3 hours.

The sulfation reaction may be illustrated by the following equation:

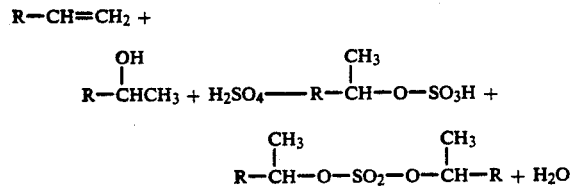

wherein R is an alkyl group having from about 6 to about 20 carbon atoms. The products of the sulfation reaction are primarily monoalkyl sulfuric acids and dialkyl sulfates along with unreacted olefin, unreacted alcohol, unreacted sulfuric acid and water.

In one embodiment, the sulfation product of step a) may, prior to the contact with a base dispersed in a nonionic surfactant in step b) or prior to neutralization, be subjected to deacidification for the partial or substantially complete removal of the unconverted sulfuric acid or any unreacted sulfating agent. Suitable deacidification procedures include washing the sulfation reaction product with water or an acid such as sulfuric acid having a concentration of from about 75 percent by weight to about 90 percent by weight, preferably from about 80 percent by weight to about 85 percent by weight, in water. The deacidification is typically carried out at the same temperature at which the sulfation reaction in step a) is carried out. However, the present invention may be carried out with or without deacidification. For example, the deacidification step is omitted when the sulfuric acid to olefin and alcohol molar ratio is less than 0.8 mole of acid/mole of olefin and alcohol, preferably 0.6 mole of acid/mole of olefin and alcohol or less.

Following the sulfation reaction in step a) and optional deacidification, the sulfation product, i.e., monoalkyl and dialkyl sulfates, is contacted with a base dispersed in a nonionic surfactant in order to neutralize the alkyl sulfuric acid portion of the sulfation product of step a) to form the corresponding sulfuric acid salts.

The neutralization reaction is accomplished using one or more bases such as ammonium or alkali metal or alkaline earth metal hydroxides or carbonates or bicarbonates dispersed in a nonionic surfactant. Suitable bases include sodium hydroxide, sodium carbonate, potassium hydroxide, calcium hydroxide and the like, with sodium hydroxide or potassium hydroxide being the preferred base. The amount of base added to the nonionic surfactant is based on the acidity of the monoalkylsulfuric acid phase after water washing and is suitably in the range of from about 1.1 meq/meq acid (milliequivalent of base per milliequivalent of acid) to about 2.5 meq/meq acid, preferably from about 1.3 meq/meq acid to about 1.9 meq/meq acid.

The neutralization procedure can be carried out over a wide range of temperatures and pressures. Typically, the neutralization procedure is carried out at a temperature in the range of from about 20° C. to about 65° C., and a pressure in the range of from about 1 atmosphere to about 2 atmospheres. The neutralization time is typically in the range of from about 0.5 hours to about 1.0 hours.

The nonionic surfactant utilized in the neutralization reaction in step b) must have a higher boiling point than the boiling point of the detergent range olefin reactant which is sulfated in step a) and its corresponding secondary alcohol. The diluent must also be a liquid or at least be sufficiently flowable to pass through a thin film evaporator. Suitable nonionic surfactants include alkyl ethoxylates and alkylaryl ethoxylates.

In a preferred embodiment, the nonionic surfactant is an alcohol ethoxylate. The general class of alcohol ethoxylates useful in the neutralization reaction in step b) as diluent is characterized by the chemical formula $R_1-O-(CH_2-CH_2O)_n-H$, wherein $R_1$ is a straight-chain or branched-chain alkyl group having in the range of from about 8 to about 18 carbon atoms, preferably from about 12 to about 18 carbon atoms, or an alkylaryl group having an alkyl moiety having from about 8 to about 12 carbon atoms, and n represents the average number of oxyethylene groups per molecule and is in the range of from about 1 to about 15, preferably from about 2 to about 12 and more preferably from about 2 to about 9. The alkyl group can have a carbon chain which is straight or branched, and the ethoxylate component can be a combination of straight-chain and branched molecules. Preferably, about 75 percent of the R groups in the instant composition are straight-chain. It is understood that R can be substituted with any substituent which is inert. Ethoxylates within this class are conventionally prepared by the sequential addition of ethylene oxide to the corresponding alcohol (ROH) in the presence of a catalyst.

The alcohol ethoxylate is preferably derived by ethoxylation of primary or secondary, straight-chain or branched alcohols. Suitably, the alcohols have from about 8 to about 18 carbon atoms, preferably from about 9 to about 15 carbon atoms, and more preferably from about 12 to about 15 carbon atoms. The most common ethoxylates in this class and the ones which are particularly useful in this invention are the primary alcohol ethoxylates, i.e., compounds of formula I in which R is an alkyl group and the $-O-(CH_2-CH_2O)_n-H$ ether substituent is bound to a primary carbon of the alkyl group.

Alcohols which are suitable to form alcohol ethoxylates for use in the present process include coconut fatty alcohols, tallow fatty alcohols, and the commercially available synthetic long-chain fatty alcohol blends, e.g. the $C_{12}$ to $C_{15}$ alcohol blends available as NEODOL 25 Alcohol (a registered trademark of product manufactured and sold by Shell Chemical Company), the $C_{12}$ to $C_{14}$ alcohol blends available as Tergitol 24 L (a registered trademark of product manufactured and sold by Union Carbide Corporation), and the $C_{12}$ to $C_{13}$ alcohol blends available, for example, as NEODOL 23 Alcohol (Shell).

Suitable alcohol ethoxylates can be prepared by adding to the alcohol or mixture of alcohols to be ethoxylated a calculated amount, e.g., from about 0.1 percent by weight to about 0.6 percent by weight, preferably from about 0.1 percent by weight to about 0.4 percent by weight, based on total alcohol, of a strong base, typically an alkali metal or alkaline earth metal hydroxide such as sodium hydroxide or potassium hydroxide, which serves as a catalyst for ethoxylation. The resulting mixture is dried, as by vapor phase removal of any water present, and an amount of ethylene oxide calculated to provide from about 0.5 mole to about 15 moles of ethylene oxide per mole of alcohol is then introduced and the resulting mixture is allowed to react until the ethylene oxide is consumed. A precalculated amount of ethylene oxide is added to achieve the desired level of ethoxylation. This amount can be readily determined by one of ordinary skill in the art with a minimal amount of experimentation. After the calculated amount of ethylene oxide has been added, the consumption of ethylene oxide can then be monitored by the decrease in reaction pressure.

The ethoxylation is typically conducted at elevated temperatures and pressures. Suitable reaction temperatures range from about 120° C. to about 220° C. with the range of from about 140° C. to about 160° C. being preferred. A suitable reaction pressure is achieved by introducing to the reaction vessel the required amount of ethylene oxide which has a high vapor pressure at the desired reaction temperature. For considerations of process safety, the partial pressure of the ethylene oxide reactant is preferably limited, for instance, to less than about 60 psig, and/or the reactant is preferably diluted with an inert gas such as nitrogen, for instance, to a vapor phase concentration of about 50 percent or less. The reaction can, however, be safely accomplished at greater ethylene oxide concentration, greater total pressure and greater partial pressure of ethylene oxide if suitable precautions, known to the art, are taken to manage the risks of explosion. A total pressure of between about 40 and 110 psig, with an ethylene oxide partial pressure between about 15 and 60 psig, is particularly preferred, while a total pressure of between about 50 and 90 psig, with an ethylene oxide partial pressure between about 20 and 50 psig, is considered more preferred. The pressure serves as a measure of the degree of the reaction and the reaction is considered to be substantially complete when the pressure no longer decreases with time.

It should be understood that the ethoxylation procedure serves to introduce a desired average number of ethylene oxide units per mole of alcohol ethoxylate. For example, treatment of an alcohol mixture with 3 moles of ethylene oxide per mole of alcohol serves to effect the ethoxylation of each alcohol molecule with an average of 3 ethylene oxide moieties per mole alcohol moiety, although a substantial proportion of alcohol moieties will become combined with more than 3 ethylene oxide moieties and an approximately equal proportion will have become combined with less than 3.

Specific nonionic surfactant compounds which can be used in the composition of the present invention include ethoxylated fatty alcohols, preferably linear primary or secondary monohydric alcohols with about $C_8$ to about $C_{18}$, preferably about $C_{12}$ to about $C_{15}$, alkyl groups and an average of about 0.5 to about 15, preferably about 0.5 to about 9, moles of ethylene oxide per mole of alcohol, and ethoxylated alkylphenols with $C_8$ to about $C_{12}$ alkyl groups, preferably about $C_8$ to about $C_{10}$ alkyl groups and an average of about 1 to about 12 moles of ethylene oxide per mole of alkylphenol.

A preferred class of nonionic ethoxylates is represented by the condensation product of a fatty alcohol having from about 12 to about 15 carbon atoms and from about 2 to about 12 moles of ethylene oxide per mole of fatty alcohol. Suitable species of this class of ethoxylates include: the condensation product of $C_{12}$–$C_{15}$ oxo-alcohols and 7 moles of ethylene oxide; the condensation product of narrow cut $C_{14}$-$C_{15}$ oxo-alcohols and 7 or 9 moles of ethylene oxide per mole of fatty (oxo)alcohol; the condensation of a narrow cut $C_{12-13}$ fatty (oxo)alcohol and 6.5 moles of ethylene oxide per mole of fatty alcohol. The fatty oxo-alcohols, while primarily linear, can have, depending upon the processing conditions and raw material olefins, a certain degree of branching. A degree of branching in the range from 15% to 50% by weight is frequently found in commercially available oxo-alcohols. Additionally, secondary alcohols may also be present.

The amount of nonionic surfactant in step b) in the present invention is such that it is sufficient to disperse in the desired base and such that the amount of nonionic surfactant in the final surfactant composition is from about 25 percent by weight to about 90 percent by weight, preferably from about 30 percent by weight to about 60 percent by weight, and more preferably from about 40 percent by weight to about 50 percent by weight. Typically, the amount of nonionic surfactant utilized in step b) is in the range of from about 35 percent by weight to about 60 percent by weight, and preferably from about 40 percent by weight to about 50 percent by weight, basis the weight of the final product.

The product may be de-salted following the neutralization reaction. A de-salting treatment may be used in place of or in addition to the de-acidification described above depending on the extent of the de-acidification. Desalting is typically carried out by using an excess of base in the neutralization reaction which neutralizes the unreacted sulfuric acid to form the inorganic salts thereof in addition to neutralizing the secondary alkyl sulfuric acids. For example, sodium sulfate may be present when sodium hydroxide is the base in the neutralization. These inorganic salts may be removed as a separate phase by known methods such as, for example, filtration. However, removal of the inorganic salts in this manner results in a loss of sulfuric acid, since the organic salts thereof are normally discarded. For this reason, removal of unreacted sulfuric acid by deacidification via water washing following sulfation is preferred.

Following the contact in step b) of the sulfation product of step a) with a base dispersed in a nonionic surfactant to effect neutralization, the product of step b), is heated in step c) to a temperature in the range of from about 70° C. to about 115° C. in order to effect saponification or hydrolysis of the dialkyl sulfates to form equimolar amounts of alkyl sulfuric acid salts and secondary alcohols. Suitably, the neutralization and saponification reactions take place by the addition of one or more bases such as amines or ammonium or alkali metal or alkaline earth metal hydroxides, carbonates or bicarbonates dispersed in a nonionic surfactant, with sodium hydroxide being the preferred base.

The saponification reaction can be carried out over a wide range of temperatures and pressures. The saponification procedure is typically carried out at a temperature in the range of from about 70° C. to about 115° C., preferably from about 80° C. to about 105° C., and a pressure of from about 1 atmosphere to about 2 atmospheres. The saponification reaction is generally carried out over a time period ranging from about 0.25 hours to about 5.0 hours.

The neutralization and saponification reactions may be illustrated by the following equations:

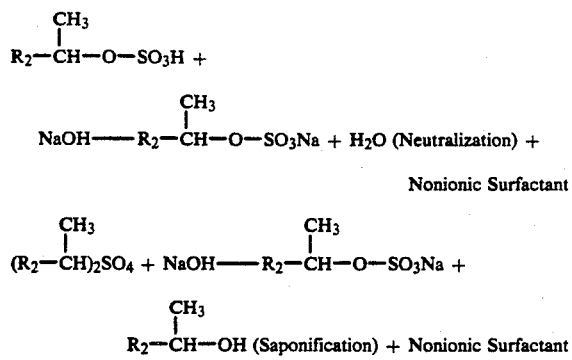

wherein $R_2$ is an alkyl group having from about 1 to about 20 carbon atoms.

Following the neutralization and saponification reactions in steps b) and c), the product of step c) is passed through a thin film evaporator in order to recover unreacted olefin and secondary alcohols. The thin film evaporator may suitably be a wiped film evaporator or a falling film evaporator. If desired, the secondary alcohol can be separated from unreacted olefin by means recognized by those skilled in the art such as, for example, distillation.

After the product is passed through an evaporator to remove unreacted organic matter, the resulting product is recovered. The product contains primarily secondary alkyl sulfate and nonionic surfactant, at least about 70 percent by weight to about 95 percent by weight, preferably about 85 percent by weight to about 95 percent by weight. The product generally contains from about 5 percent by weight to about 75 percent by weight, preferably from about 20 percent by weight to about 60 percent by weight secondary alkyl sulfate, and from about 25 percent by weight to about 90 percent weight, preferably from about 30 percent by weight to about 60 percent by weight nonionic surfactant. Some residual level of sodium sulfate remains. The product typically contains less than about 12 percent by weight, preferably less than about 9 percent by weight, sodium sulfate.

The weight ratio of secondary alkyl sulfate to nonionic surfactant in the resulting surfactant composition can vary widely with weight ratios in the range of from about 0.1:1 to about 4:1, preferably from about 1:3 to about 3:1, and more preferably, from about 1:1 to about 2:1.

Typically, the compositions of the invention have a surface active material content after thin film evaporation, i.e. the percentage of secondary alkyl sulfate and primary alkyl sulfate plus the percentage of nonionic surfactant, of at least about 70 percent by weight, preferably at least about 85 percent by weight, and more preferably, at least about 90 percent by weight of said composition. The compositions also contain from about 5 percent by weight to about 10 percent by weight sodium sulfate.

The surfactant compositions of the invention can be utilized in a variety of detergent applications. The surfactant compositions can be adsorbed at relatively low temperatures, about 85° C. or less, onto solid detergent materials such as, for example, sodium carbonate, in order to form dry detergent powders. The surfactant compositions can also be added to water or vice versa in order to form liquid detergents.

When an alcohol ethoxylate is used as the nonionic surfactant in the instant process, the surfactant compositions prepared may suitably be a detergent formulation of the general sort as is conventionally made of ethoxylate-containing surfactant compositions. Commonly, but not necessarily, such a formulation would contain the surfactant composition of the instant invention in a quantity between about one and about fifty percent by weight. The remainder of such formulation would be comprised of one or more additional components which are conveniently used in ethoxylatecontaining formulations, such as, for example, water; detergent builders; sequestering agents; coloring agents; enzymes; perfumes; and other nonionic and anionic as well as cationic detergent active materials.

The ranges and limitations provided in the instant specification and claims are those which are believed to particularly point out and distinctly claim the present invention. It is, however, understood that other ranges and limitations which perform substantially the same function in substantially the same manner to obtain the same or substantially the same result are intended to be within the scope of the instant invention as defined by the instant specification and claims.

The invention will be described below by the following examples which are provided for purposes of illustration and are not to be construed as limiting the invention.

Illustrative Embodiments

EXAMPLE 1

Preparation of Surfactant Compositions

Sulfation

To a round-bottomed flask equipped with a paddle stirrer, thermometer, and addition funnel topped with a nitrogen blanket was added 250.00 grams of $C_{14/17}$ internal olefin ($C_{14}$, 3.4% weight (%w); $C_{15}$, 41.8%w; $C_{16}$, 36.5%w; $C_{17}$, 15.3%w; and $C_{18}$, 3.0%w) and 26.96 grams of 2-hexadecanol. After cooling to 17° –19° C., 76.70 grams of 95% sulfuric acid was added at such a rate that the temperature was maintained at 17° –19° C. When acid addition was complete, acidity was monitored by titration until it remained essentially constant.

Neutralization/Saponification

The mixture from the sulfation above (350.48 grams) was added to a stirred mixture of 140 grams of Neodol 23-6.5 alcohol ethoxylate (NEODOL is a trademark of Shell Chemical Company) and 89.24 grams of 50 percent by weight (%w) sodium hydroxide, at 24° –61° C. over a period of eighteen minutes. The alkalinity was 0.61 milliequivalents/gram (meq/g) after neutralization.

After neutralization, the mixture was heated with stirring to reflux (approximately 105° C.) and held at reflux for about one hour.

A sample after about one hour at reflux gave an anionic concentration of 91.23 meq/100 grams. The alkalinity after one hour was 0.26 meq/gram.

Thin Film Evaporation

To a wiped film evaporator at 140° –141° C. and about 50 mm Hg pressure, was added 548.63 grams of the neutralized/saponified product from the above step. The wiped film evaporator distillation required twenty-five minutes and produced 470.43 grams of bottoms product. The distillate was a mixture of water and unreacted organic matter, amounting to 59.80 g.

456.59 Grams of the bottoms produced above in the first wiped film evaporator distillation was added to a wiped film evaporator at 141° –142° C. and about 30 mm Hg pressure over a period of about forty minutes. 350.01 Grams of bottoms product and 96.57 g of water and unreacted organic matter distillate were produced.

The bottoms product was redistilled through the wiped film evaporator at 140° C. and a vacuum of 0.25–0.4 mm Hg two times until anionic reached a concentration of 138.8 meq/100 g or 47.7%w.

EXAMPLE 2

Preparation of Surfactant Compositions

Sulfation

The reaction was carried out as described in Example 1 above with 76.88 grams of 95% sulfuric acid added to a well stirred mixture of 250.00 grams of $C_{14/17}$ internal olefin ($C_{14}$, 3.4% weight (%w); $C_{15}$, 41.8%w; $C_{16}$, 36.5%w; $C_{17}$, 15.3%w; and $C_{18}$, 3.0%w) and 26.96 grams of Neodol 23-1 alcohol ethoxylate at 17° –25° C. When acid addition was complete, acidity was monitored by titration until it remained essentially constant.

Neutralization/Saponification

The mixture from the sulfation above (350.33 grams) was added to a stirred mixture of 96.53 grams of 50%w NAOH and 140.00 of Neodol 23-6.5 alcohol ethoxylate at 27° –60° C.

After neutralization, the mixture was heated with stirring to about 100° –109° C. and held until anionic titration held essentially constant at about 84.8 meq/100g or 28.8 % w anionic.

Thin Film Evaporation

To a wiped film evaporator at 139° –140° C. and about 47–49 mm Hg was added 547.25 grams of the neutralization/saponification product from above. The wiped film evaporator distillation required 39 minutes and produced 466.54 grams of bottoms product. The distillate was a mixture of water and unreacted organic matter, amounting to 59.23 grams. The wiped film evaporator distillation of the bottoms product was carried out two additional times at 140° –141° C. and vacuums of about 1.2 and about 0.2–0.35 mm Hg, respectively, producing 89.05 grams of product having an anionic content of about 40%w (116.3 meq/100g).

EXAMPLE 3

Preparation of Surfactant Compositions

Sulfation

The reaction was carried out as described in Example 1 above with 12.88 grams of 95% sulfuric acid added to a well stirred mixture of 50.00 grams of 2-hexadecanol and 50.00 grams of n-heptane at 25° –30° C. When acid addition was complete, acidity was monitored by titration until it remained essentially constant.

Neutralization/Saponification

The mixture from the sulfation above (103.27 grams) was added to a stirred mixture of 15.70 grams of 50%w NAOH and 96.40 grams of Neodol 23-6.5 at 31° –40° C.

After neutralization, the mixture was heated with stirring to about 89° –91° C. for about 1-hr. after which a Dean-Stark trap was added to the reaction flask and water was removed by azeotropic distillation. Anionic titration gave 36.2 meq/100 g or 12.5%w anionic.

Thin Film Evaporation

To a wiped film evaporator at about 141° C. and about 0.26–0.40 mm Hg was added 167.23 grams of the neutralization/saponification product from above. The wiped film evaporator distillation required 21 minutes and produced 119.32 grams of bottoms product. The distillate was a mixture of heptane and unreacted organic matter, amounting to 29.31 grams. The wiped film evaporator distillation of the bottoms product was carried out 2-additional times at 140° –141° C. and vacuum of about 0.25–0.31 mm. Hg., producing 68.72 grams of product having an anionic content of about 19%w (54 meq/100g).

What is claimed is:

1. A process for preparing secondary alkyl sulfate-containing surface active compositions substantially free of unreacted organic matter and water, which process comprises: a) sulfating a mixture of a detergent range olefin having from about 8 to about 22 carbon atoms and a detergent range alcohol having from about 8 to about 22 carbon atoms with a sulfating agent, b) neutralizing the product of step a) with a base dispersed in a nonionic surfactant having a boiling point higher than that of said detergent range olefin and its corresponding secondary alcohol, c) saponifying the product of step b), d) passing the product of step c) through a thin film evaporator to evaporate unreacted organic matter from said product and recovering said product.

2. The process of claim 1 wherein said detergent range olefin has from about 12 to about 18 carbon atoms.

3. The process of claim 1 wherein said detergent range alcohol has from about 12 to about 18 carbon atoms.

4. The process of claim 3 wherein said detergent range alcohol is an ethoxylated alcohol having from about 12 to about 15 carbon atoms and from about 0.5 to about 9 moles of ethylene oxide per mole of alcohol.

5. The process of claim 1 wherein said sulfating agent is concentrated sulfuric acid having a concentration in the range of from about 75 percent by weight to about 100 percent by weight in water.

6. The process of claim 1 wherein said sulfation in step a) is carried out at a temperature in the range of from about 5° C. to about 40° C. and a pressure in the range of from about 1 atmosphere to about 2 atmospheres.

7. The process of claim 1 wherein following step a), the product of step a) is subjected to deacidification by water washing.

8. The process of claim 1 wherein said base in step b) is selected from amines or ammonium, alkali metal or alkaline earth metal hydroxides, carbonates or bicarbonates.

9. The process of claim 1 wherein said base is sodium hydroxide.

10. The process of claim 1 wherein said nonionic surfactant in step b) is an alcohol ethoxylate having a formula $R_1-O-(CH_2CH_2O)_n-H$, wherein $R_1$ is an alkyl group having from about 8 to about 18 carbon atoms or an arylalkyl group having an alkyl moiety having from about 8 to about 12 carbon atoms, and n represents the average number of oxyethylene groups per molecule and is a number in the range of from about 1 to about 12.

11. The process of claim 1 wherein said neutralization in step b) is carried out at temperatures in the range of 12. The process of claim 1 wherein said saponification in step c) is carried out at a temperature in the range of from about 80° C. to about 105° C. and a pressure of from about 1 atmosphere to about 2 atmospheres.

13. The process of claim 1 wherein in step d), said thin film evaporator is a wiped film evaporator.

14. The process of claim 1 wherein said product recovered in step d) contains from about 5 percent by weight to about 75 percent by weight secondary alkyl sulfate and from about 25 percent by weight to about 90 percent by weight nonionic surfactant.

15. The process of claim 14 wherein said product recovered in step d) contains from about 20 percent by weight to about 60 percent by weight secondary alkyl sulfate and from about 30 percent by weight to about 60 percent by weight nonionic surfactant.

16. The process of claim 10 wherein said product recovered in step d) contains from about 5 percent by weight to about 75 percent by weight secondary alkyl sulfate and from about 25 percent by weight to about 90 percent by weight alcohol ethoxylate.

17. The process of claim 16 wherein said product recovered in step d) contains from about 20 percent by weight to about 60 percent by weight secondary alkyl sulfate and from about 30 percent by weight to about 60 percent by weight alcohol ethoxylate.

18. A process for preparing secondary alcohol sulfate-containing surface active compositions substantially free of unreacted organic matter and water, which process comprises: a) sulfating a mixture of a detergent range olefin having from about 8 to about 22 carbon atoms and a detergent range alcohol having from about 8 to about 22 carbon atoms with a sulfating agent, b) neutralizing the product of step a) with a base dispersed in an alcohol ethoxylate having a formula $R_1-O-(CH_2CH_2O)_n-H$, wherein $R_1$ is an alkyl group having from about 8 to about 18 carbon atoms or an arylalkyl group having an alkyl moiety having from about 8 to about 12 carbon atoms, and n represents the average number of oxyethylene groups per molecule and is a number in the range of from about 1 to about 12, said alcohol ethoxylate having a boiling point higher than that of said detergent range olefin and its corresponding secondary alcohol, c) saponifying the product of step b), d) passing the product of step c) through a thin film evaporator to evaporate unreacted organic matter and recovering said product.

19. The process of claim 18 wherein said detergent range olefin has from about 12 to about 18 carbon atoms.

20. The process of claim 18 wherein said detergent range alcohol has from about 12 to about 18 carbon atoms.

21. The process of claim 20 wherein said detergent range alcohol is an ethoxylated alcohol having from about 12 to about 15 carbon atoms and from about 0.5 to about 9 moles of ethylene oxide per mole of alcohol.

22. The process of claim 18 wherein said sulfating agent is concentrated sulfuric acid having a concentration in the range of from about 85 percent by weight to about 98 percent by weight in water.

23. The process of claim 18 wherein said sulfation in step a) is carried out at a temperature in the range of from about 5° C. to about 40° C. and a pressure in the range of from about 1 atmosphere to about 2 atmospheres.

24. The process of claim 18 wherein following step a), the product of step a) is subjected to deacidification by water washing.

25. The process of claim 18 wherein said base in step b) is selected from amines or ammonium, alkali metal or alkaline earth metal hydroxides, carbonates or bicarbonates.

26. The process of claim 25 wherein said base is sodium hydroxide.

27. The process of claim 18 wherein said neutralization in step b) is carried out at temperatures in the range of from about 20° C. to about 65° C. and pressures in the range of from about 1 atmosphere to about 2 atmospheres.

28. The process of claim 18 wherein said saponification in step c) is carried out at a temperature in the range of from about 80° C. to about 105° C. and a pressure of from about 1 atmosphere to about 2 atmosphere.

29. The process of claim 18 wherein in step d), said thin film evaporator is a wiped film evaporator.

30. The process of claim 18 wherein said product recovered in step d) contains from about 5 percent by weight to about 75 percent by weight secondary alkyl sulfate and from about 25 percent by weight to about 90 percent by weight alcohol ethoxylate.

31. The process of claim 30 wherein said product recovered in step d) contains from about 20 percent by weight to about 60 percent by weight secondary alkyl sulfate and from about 30 percent by weight to about 60 percent by weight alcohol ethoxylate.

32. The process of claim 18 wherein said composition contains at least about 85 percent by weight of secondary alkyl sulfate and alcohol ethoxylate.

* * * * *